United States Patent
Peters et al.

(10) Patent No.: US 9,636,344 B2
(45) Date of Patent: *May 2, 2017

(54) SUBSTITUTED 2,3-DIHYDROIMIDAZO[1,2-C]QUINAZOLINE SALTS

(71) Applicant: Bayer Intellectual Property GmbH, Monheim (DE)

(72) Inventors: Jan-Georg Peters, Solingen (DE); Hans-Christian Militzer, Odenthal (DE); Hartwig Müller, Velbert (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/990,350

(22) Filed: Jan. 7, 2016

(65) Prior Publication Data
US 2016/0193219 A1    Jul. 7, 2016

Related U.S. Application Data

(63) Continuation of application No. 14/009,599, filed as application No. PCT/EP2012/055600 on Mar. 29, 2012, now abandoned.

(30) Foreign Application Priority Data

Apr. 5, 2011   (EP) ...................... 11161111

(51) Int. Cl.
A61K 31/5377   (2006.01)
C07D 487/04    (2006.01)
A61K 45/06     (2006.01)

(52) U.S. Cl.
CPC .......... *A61K 31/5377* (2013.01); *A61K 45/06* (2013.01); *C07D 487/04* (2013.01)

(58) Field of Classification Search
CPC .................................. A61K 31/5377
See application file for complete search history.

(56) References Cited

U.S. PATENT DOCUMENTS

| | | |
|---|---|---|
| 4,140,707 A | 2/1979 | Cleare et al. |
| 5,521,184 A | 5/1996 | Zimmermann |
| 5,665,772 A | 9/1997 | Cottens et al. |
| 7,511,041 B2 | 3/2009 | Shimada et al. |
| 8,129,386 B2 | 3/2012 | Shimada et al. |
| 8,466,283 B2 | 6/2013 | Hentemann et al. |
| 8,568,720 B2 | 10/2013 | Morichika et al. |
| 8,859,572 B2 | 10/2014 | Hentemann et al. |

FOREIGN PATENT DOCUMENTS

| | | |
|---|---|---|
| DE | 2329485 | 12/1973 |
| EP | 0 564 409 | 10/1993 |
| EP | 2 168 582 A1 | 3/2010 |
| EP | 2168582 A1 | 3/2010 |
| NL | 7307863 | 12/1973 |
| WO | 94/09010 A1 | 4/1994 |
| WO | 02/20519 A1 | 3/2002 |
| WO | 2004/029055 A1 | 4/2004 |
| WO | 2008/070150 A1 | 6/2008 |
| WO | 2010/034414 A1 | 4/2010 |
| WO | 2010/070370 A1 | 6/2010 |
| WO | 2011/128407 A2 | 10/2011 |
| WO | 2012/062748 A1 | 5/2012 |

OTHER PUBLICATIONS

The Merck Index: "An encyclopedia of chemicals, drugs, and biological" 15th Edition, 2013, pp. 910-911 and p. 718.
Carlos Correa. "Guidelines for the Examination of Pharmaceutical Patents: Developing a Public Health Perspective"; University of Buenos Aires; published by International Centre for Trade and Sustainable Development (ICTSD), World Health Organization (WHO), Switzerland 2007, p. 9.
Giron, D., "Thermal analysis and calorimetric methods in the characterisation of polymorphs and solvates," Thermochimica Acta, 1995, 248:1-59.
Torbett Neil E et al., "A chemical screen in diverse breast cancer cell lines reveals genetic enhancers and suppressors of sensitivity to PI3K", Biochem. J., 2008, 415:97-110.
U.S. Appl. No. 14/500,484, filed Sep. 29, 2014, Examiner: Gembeh, Shirley V.
U.S. Appl. No. 14/009,751, filed May 19, 2014, Examiner: Rao, Savitha M.
U.S. Appl. No. 13/908,566, filed Jun. 3, 2013, Examiner Stone, Christopher R.
U.S. Appl. No. 12/812,911, filed Apr. 18, 2011, now U.S. Pat. No. 8,859,572, issued Oct. 14, 2014.

*Primary Examiner* — Noble Jarrell
*Assistant Examiner* — John S Kenyon
(74) *Attorney, Agent, or Firm* — Morrison and Foerster LLP

(57) ABSTRACT

The present invention relates
to 2-amino-N-[7-methoxy-8-(3-morpholin-4-ylpropoxy)-2,3-dihydroimidazo-[1,2-c]quinazolin-5-yl]pyrimidine-5-carboxamide dihydrochloride salt of formula (II):

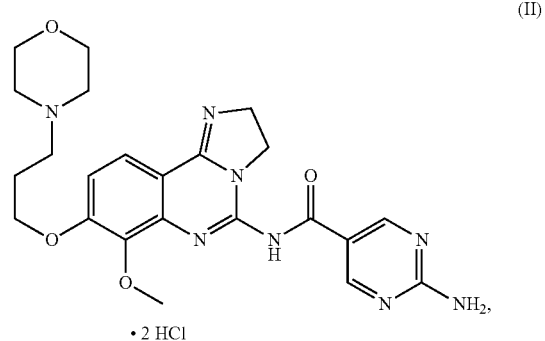

or a tautomer, solvate or hydrate thereof; and to its use for the treatment of non-Hodgkin's lymphoma.

4 Claims, 7 Drawing Sheets

IR spectrum of the dihydrochloride of formula (II)

Raman spectrum of the dihydrochloride of formula (II)

UV/VIS spectra of the dihydrochloride of formula (II)

¹H-NMR Spectrum of the dihydrochloride of formula (II)

13C-NMR Spectrum of the dihydrochloride of formula (II)

$^{13}$C-NMR Spectra of the dihydrochloride of formula (II)

Mass Spectrum of the dihydrochloride of formula (II)

SUBSTITUTED 2,3-DIHYDROIMIDAZO[1,2-C]QUINAZOLINE SALTS

The present invention relates:
to 2-amino-N-[7-methoxy-8-(3-morpholin-4-ylpropoxy)-2,3-dihydroimidazo-[1,2-c]quinazolin-5-yl]pyrimidine-5-carboxamide dihydrochloride salt of formula (II):

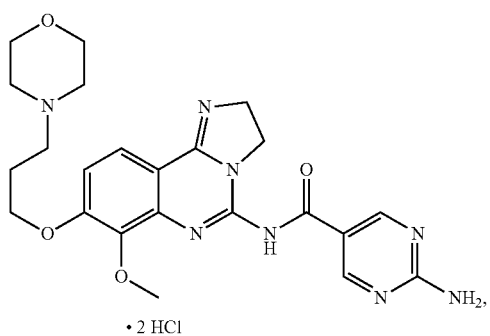

or a tautomer, solvate or hydrate thereof,
(which is hereinafter referred to as "the salt of the present invention" or the "dihydrochloride salt");
  to methods of preparing said salt of the present invention;
  to said salt of the present invention for the treatment and/or prophylaxis of a disease;
  to the use of said salt of the present invention for the preparation of a medicament for the treatment and/or prophylaxis of a disease, in particular of a hyperproliferative and/or angiogenesis disorder, more particularly for the treatment or prophylaxis of a cancer, particularly lung cancer, in particular non-small cell lung carcinoma, colorectal cancer, melanoma, pancreatic cancer, hepatocyte carcinoma, or breast cancer;
  to a pharmaceutical composition comprising said salt of the present invention; and
  to a pharmaceutical combination comprising said salt of the present invention in combination with one or more further pharmaceutical agents.

BACKGROUND TO THE INVENTION

The compound of formula (I):

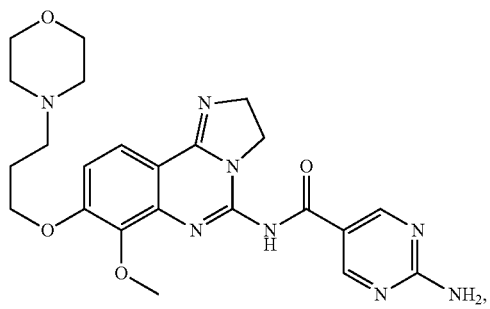

(which is hereinafter referred to as the "compound of formula (I)" or the "free base"), is a proprietary cancer agent with a novel mechanism of action, inhibiting Class I phosphatidylinositol-3-kinases (PI3Ks). This class of kinases is an attractive target since PI3Ks play a central role in the transduction of cellular signals from surface receptors for survival and proliferation. The compound of formula (I) exhibits a broad spectrum of activity against tumours of multiple histologic types, both in vitro and in vivo.

Said compound of formula (I) may be synthesised according to the methods given in international patent application PCT/EP2003/010377, published as WO 04/029055 A1 on Apr. 8, 2004, (which is incorporated herein by reference in its entirety), on pp. 26 et seq.

Moreover, said compound of formula (I) is published in international patent application PCT/US2007/024985, published as WO 2008/070150 A1 on Jun. 12, 2008, (which is incorporated herein by reference in its entirety), as the compound of Example 13: 2-amino-N-[7-methoxy-8-(3-morpholin-4-ylpropoxy)-2,3-dihydroimidazo[1,2-c]quinazolin-5-yl]pyrimidine-5-carboxamide. Further, said compound of formula (I) is, in WO 2008/070150, described on pp. 9 et seq., and may be synthesized according to the methods given therein on pp. 42 et seq. Biological test data for said compound of formula (I) is given therein on pp. 101 to 107.

Said compound of formula (I) may exist in one or more tautomeric forms: tautomers, sometimes referred to as proton-shift tautomers, are two or more compounds that are related by the migration of a hydrogen atom accompanied by the migration of one or more single bonds and one or more adjacent double bonds.

The compound of formula (I) may for example exist in tautomeric form (Ia), tautomeric form (Ib), or tautomeric form (Ic), or may exist as a mixture of any of these forms, as depicted below. It is intended that all such tautomeric forms are included within the scope of the present invention.

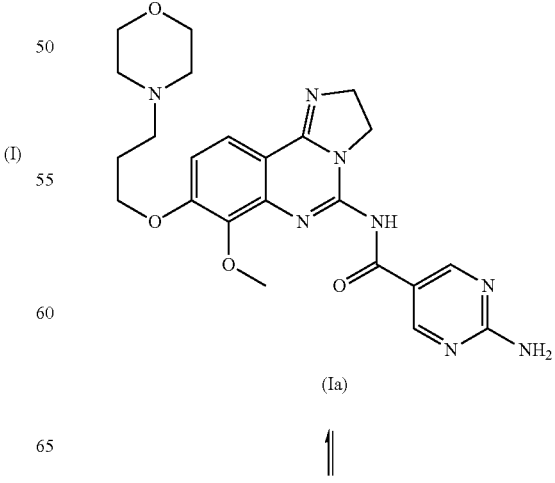

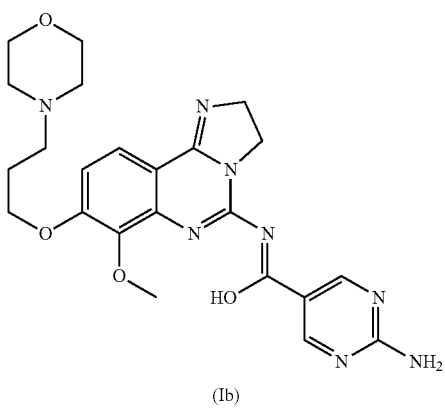

(Ib)

⇅

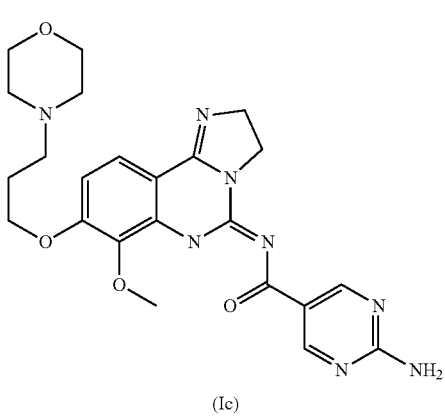

(Ic)

Said compound of formula (I) may exist as a solvate: a solvate for the purpose of this invention is a complex of a solvent and a compound of formula (I) in the solid state. Exemplary solvates include, but are not limited to, complexes of a compound of the invention with ethanol or methanol.

Said compound of formula (I) may exist as a hydrate: Hydrates are a specific form of solvate wherein the solvent is water.

Technical Problem to be Solved

In general, for a given pharmaceutically active compound, pharmaceutically acceptable forms of said given pharmaceutically active compound are desired, with the view to increasing the pharmaceutical effectiveness of said pharmaceutically active compound, e.g. improving physical chemical characteristics, such as chemical stability, physical stability, solubility in vivo, improving absorption of the pharmaceutically active compound in vivo, etc. In addition, a drug substance would ideally come in a stable crystal form that can be produced in a reliable way. Amorphous or crystal forms of low order (e.g. mesomorphic forms) are less attractive as they carry the risk of a later form change and changes of physical properties.

However, said compound of formula (I) (which is a free base) could only be prepared in a mesomorphic form that is stable in solid form, but unstable at 70° C. in acidic aqueous solution and carries the above mentioned risk of a later form change.

The formation of a crystalline salt form of the free base (I) might solve the above mention problem once the properties of this form are advantageous with respect to the properties of the free base (I). In our efforts to prepare crystalline salt forms of (I) we experienced that preparing crystalline salt forms of (I) is not as easy as one might expect for a compound carrying basic centers.

Furthermore, the compound of formula (I) exhibits very low solubility in water and most organic solvents. With two very basic centres (Table I, vide infra), solubility is strongly improved in acidic media. Consequently, purification of and final processing of the compound of formula (I) is a challenging task.

The following structure shows the compound of formula (I), on which calculated pKa values have been given in parentheses.

COMPOUND of FORMULA (I)

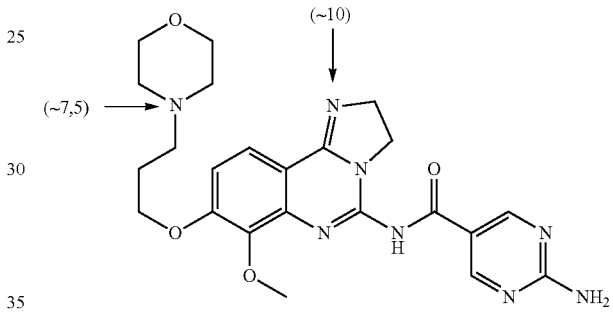

TABLE I pKa values of the compound of formula (I):

| funct. group/pKa values | experimental | calculated |
|---|---|---|
| pKa (Imidazolinoamindine) | — | 10.1 |
| pKa (Morpholine) | — | 7.43-7.5 |
| pKa (Aminopyrimidine) | — | 1.99-2.11 |

More particularly, with regard to the unique chemical structure of the compound of formula (I), vide supra, the physical properties of the compound of formula (I) are not only challenging with regard to the chemical process, the handling of the drug substance and the production of drug product, but additionally offer significant challenges for the development of a stable and reliable HPLC method as well.

It would be desirable to have a pharmaceutically acceptable and crystalline form of the compound of formula (I) which allows its reliable purification, e.g., by crystallization, in view of the difficult, specific technical problems and very low aqueous solubility, and which is easy to handle (e.g., which is a free-flowing solid).

Solution to the Technical Problem

Various attempts were made to prepare crystalline salts of the compound of formula (I). The formation of crystalline salt forms proved to be difficult, as in general no solution was achieved and in several cases gum-like, sticky materials were formed.

Unexpectedly, and this represents a basis of the present invention, it has been discovered that the dihydrochloride salt of the compound of formula (I), of the present invention (no specific disclosure of which is known to the Applicant's knowledge in the prior art), possesses technically advantageous properties, as seen inter alia in the Experimental Section and Conclusion Section of this text.

The present invention thus relates:

to 2-amino-N-[7-methoxy-8-(3-morpholin-4-ylpropoxy)-2,3-dihydroimidazo-[1,2-c]quinazolin-5-yl]pyrimidine-5-carboxamide dihydrochloride salt of formula (II):

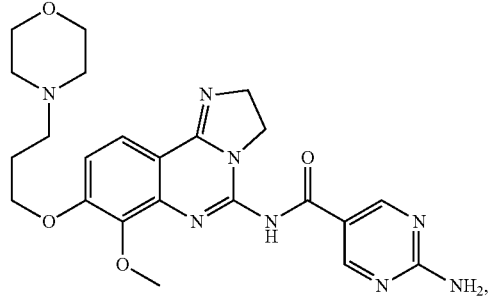
(I)

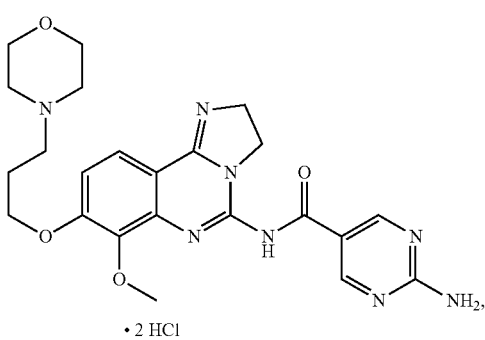
(II)

preferably in suspension,
thereby forming said dihydrochloride salt of formula (II):

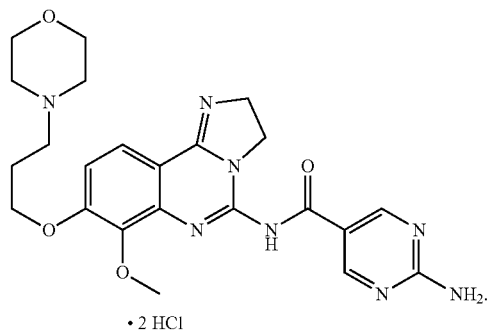
(II)

or a tautomer, solvate or hydrate thereof, (which is hereinafter referred to as "the salt of the present invention" or the "dihydrochloride salt");

to methods of preparing said salt of the present invention;

to said salt of the present invention for the treatment and/or prophylaxis of a disease;

to the use of said salt of the present invention for the preparation of a medicament for the treatment and/or prophylaxis of a disease, in particular of a hyperproliferative and/or angiogenesis disorder, more particularly for the treatment or prophylaxis of a cancer, in particular non-small cell lung carcinoma, colorectal cancer, melanoma, pancreatic cancer, hepatocyte carcinoma or breast cancer;

to a pharmaceutical composition comprising said salt of the present invention; and to a pharmaceutical combination comprising said salt of the present invention in combination with one or more further pharmaceutical agents.

Methods of Preparing the Salt of the Present Invention

The present invention also relates to a method of preparing the dihydrochloride salt of formula (II) of the present invention, which involves the addition of hydrochloric acid to the compound of formula (I), or, inversely, the addition of the compound of formula (I) to hydrochloric acid.

In accordance with an embodiment of the present invention, said method of preparing the dihydrochloride salt of formula (II) of the present invention comprises adding hydrochloric acid to a compound of formula (I):

In accordance with an embodiment of the present invention, said method of preparing the dihydrochloride salt of formula (II) of the present invention comprises:

a) adding hydrochloric acid, such as aqueous hydrochloric acid solution (32%) for example, to a suspension of said compound of formula (I) in a medium, such as water for example, at a temperature of between the freezing point of the mixture and the boiling point of the mixture, such as at a temperature of 20° C. (+−2°), until a pH of 3 to 4 is reached;

b) stirring the resulting mixture at a temperature of between the freezing point of the mixture and the boiling point of the mixture, such as at room temperature for example, for a period of time, such as for more than 10 minutes for example; and, optionally c) filtering off the resulting solid and washing the filtercake, such as with water for example, then adjusting the pH of the filtrate to pH 1.8 to 2.0 using hydrochloric acid, such as aqueous hydrochloric acid solution (32%) for example; and, optionally, d) stirring the mixture for a period of time, such as 10 minutes for example, at a temperature between the freezing point and the boiling point of the mixture, such as at room temperature for example, adding ethanol, followed by further stirring for a period of time, such as for 10 minutes for example; and, optionally, e) adding seed crystals, optionally followed by adding ethanol over a period of time such as within 5 hours for example; and, optionally, f) filtering off the resulting dihydrochloride of formula (II), optionally washing with a water-ethanol mixture and optionally drying, such as in vacuo for example, thus providing the dihydrochloride salt of formula (II) of the present invention.

In accordance with an embodiment of the present invention, said method of preparing the dihydrochloride salt of formula (II) of the present invention comprises:
a) adding said hydrochloric acid to said compound of formula (I) in acetone/water or ethanol/water for example; and, then, optionally,
b) heating at a temperature between the boiling point and the freezing point of the mixture, such as at 40 to 60° C. for example, such as at 50° C. for example, for a period of time preferably of 0.2 to 2 hours for example, such as for 0.5 hours for example; then, optionally,
c) heating further at a temperature between the boiling point and the freezing point of the mixture, such as at 30 to 40° C. for example, such as at 35° C. for example, for a period of time such as 1 to 4 hours for example, with optional stirring of said suspension at a temperature of between the boiling point and the freezing point of the mixture, such as 10 to 45° C. for example, such as at 35° C. for example, for a period of time preferably 12 to 72 hours for example, such as for 72 hours for example, optionally followed by stirring said suspension at a temperature of between the freezing point of the mixture and the boiling point of the mixture, such as at room temperature for example, for a period of time of 0 to 4 hours, such as 2 hours for example; and, optionally,
d) filtering, optional washing and drying,
thus providing the dihydrochloride salt of formula (II) of the present invention.

In accordance with an embodiment of the present invention, said method of preparing the dihydrochloride salt of formula (II) of the present invention is as follows:

said hydrochloric acid is concentrated aqueous hydrochloric acid solution (1.33 g, 36% HCl) and is added to said compound of formula (I) in an acetone/water mixture (50 mL, 8:2 v/v), followed by heating at a temperature of 50° C., for a period of time of 0.5 hours, then followed by further heating, at a temperature of 35° C., for a period of time of 72 hours, then with stirring of said suspension at a temperature of room temperature, for a period of time of 2 hours, followed by filtration, washing with an acetone/water mixture, and drying in a vacuum oven (40° C., 100 mbar, 16 h), thus providing said dihydrochloride salt of formula (II) of the present invention.

EXPERIMENTAL SECTION

Figure 1:
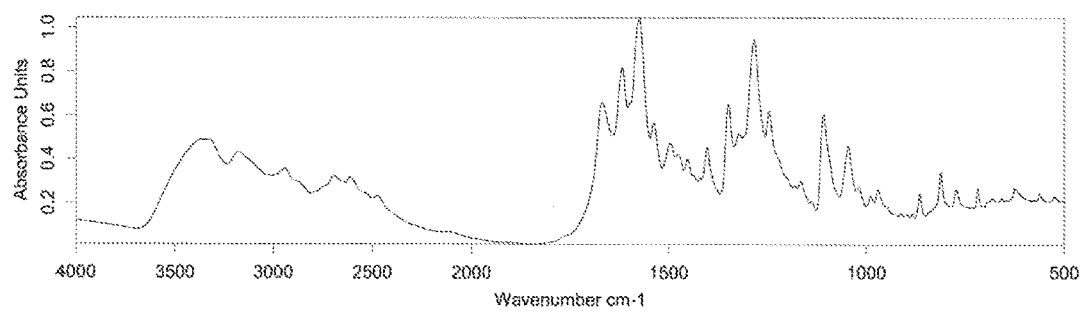
FIG. 1 shows an IR spectrum of the dihydrochloride of formula (II).

The following terms and abbreviations are used in the following text:

"compound of formula (I)" or "free base" means 2-amino-N-[7-methoxy-8-(3-morpholin-4-ylpropoxy)-2,3-dihydroimidazo[1,2-c]quinazolin-5-yl]pyrimidine-5-carboxamide of formula (I):

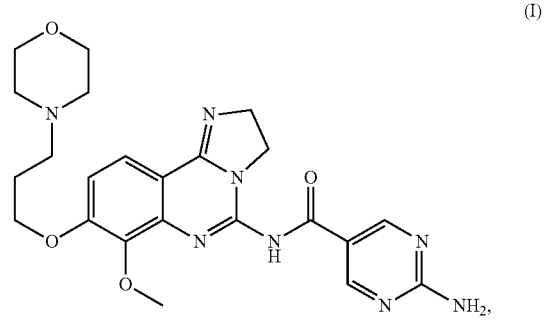 [SMILES: COc1c(OCCCN2CCOCC2)ccc2c1N=C(NC(=O)c1cnc(N)nc1)N1CCN=C21]

which is the compound of Example 13 of WO 2008/070150 A1 as indicated vide supra.

"DS" means "drug substance", i.e., the "compound of formula (I)" or "free base"

"dihydrochloride salt of formula (II)" or "salt of formula (II)" means 2-amino-N-[7-methoxy-8-(3-morpholin-4-ylpropoxy)-2,3-dihydroimidazo[1,2-c]quinazolin-5-yl]pyrimidine-5-carboxamide dihydrochloride, which is the dihydrochloride salt of formula (II):

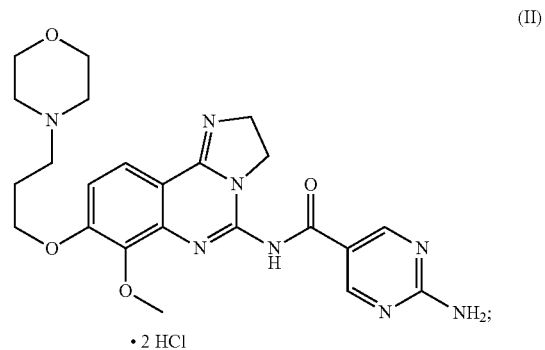 [SMILES: COc1c(OCCCN2CCOCC2)ccc2c1N=C(NC(=O)c1cnc(N)nc1)N1CCN=C21]

"NMP" means N-Methylpyrrolidinone (solvent):

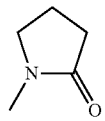

"XRPD" means "X-ray powder diffraction": the apparatus used for measurements mentioned is the following:
STOE Powder Diffraction System:
Diffractometer: Transmission
Monochromator: Curved Germanium (111)
Generator: 45 kV, 35 mA
Wavelength: 1.540598 Cu
Detector: Linear PSD
Scan Mode: Transmission/Moving PSD/Fixed omega Scan Type: 2Theta:Omega
Room conditions: 25° C., 40-60% rF
"IC" means "Ion Chromatography":
  Machine: Merck Ion Chromatograph with Suppressor System
  Detection: Conductivity detector, Fa. Metrohm
"TGA" means "Thermogravimetric Analysis":
  Machine: Thermogravimetric Analyzer TGA 7 or TGA 850e
  Producer: Perkin Elmer or Mettler-Toledo
  Heating rate: 10 Kmin$^{-1}$ or 5 K/min
  Flushing gas (Spülgas): nitrogen, 20-30 ml/min
  Crucible (Tiegel): open platinum crucible (offener Platin-Tiegel)
  Sample preparation: none
"DSC" means "Differential Scanning calorimetry":
  Machine: Differential Scanning calorimeter DSC 7 or Pyris-1 or DSC 821e
  Producer: Perkin-Elmer or Mettler-Toledo
  Heating rate: 2 and 20 K/min or 5 K/min
  Flushing gas (Spülgas): nitrogen
  Crucible (Tiegel): non-gas tight aluminium crucible
  Sample preparation: none
"DVS" means "Dynamic Vapour Sorption":
  Machine: Dynamic Vapour Sorption Analyzer IGA Sorp from the firm Hiden Analytical.
  The operating temperature was 25° C. Sample preparation: none.
"Pred." or "predom." means "predominantly".
  Overall CD: (subjective) judgement with regard to overall chemical developability.

Example 1: Dihydrochloride Salt of Formula (II)

To a suspension of the compound of formula I (3 g) in an acetone/water mixture (50 mL, 8:2 v/v) was added a concentrated aqueous hydrochloric acid solution (1.33 g, 36% HCl) resulting in no visible changes. The resulting mixture was stirred at 50° C. for 0.5 h, followed by 35° C. for 3 days, then room temperature for 2 h. The resulting solid material was isolated by filtration, washed with an acetone/water mixture (8:2 v/v) and dried in a vacuum oven (40° C., 100 mbar, 16 h) to give the desired material (3.2 g, 93% yield). Note: the solids had actuable filtration characteristics.

Characterization:

| analytical method | Results | Comments |
| --- | --- | --- |
| HPLC, wt % DS | 72.8 wt %, ~97.8% area %, sum of impurities ~2.2% | Quality significantly improved with regard to Batch A |
| IC, wt % salt former | 10.3 wt % | ~1:2-salt |
| TGA | 13.8% up to 70° C. | |
| DSC | broad peaks (60°, 120° C.) | |
| XRPD | crystalline | differences prob. due to solvent integration |
| Microscopy | Microcrystalline, agglomerates | |

XRPD results are consistent with the solids formed being crystalline.
IC results are consistent with formation of the dihydrochloride.
TGA results are consistent with the solids containing 13-14% solvent and/or water.
Analytical HPLC wt % DS is consistent with dihydrochloride solids containing 13-14% solvent and/or water. The HPLC area integration shows 2,2% impurity.

Stability as Solid:

The dihydrochloride of formula (II) (100 mg from Example 4) was stored at 90° C. for 1 week, then analyzed by HPLC.

| analytical method | results | Comments |
| --- | --- | --- |
| HPLC, wt % DS | ~65.6 wt % | |
| HPLC, area % DS | ~98.2%; sum of impurities ~1.8% | Stable |

Aqueous Solubility:

The dihydrochloride of formula (II) (500 mg from Example 4) was stirred at 25° C. for 20 h in water (5 mL). The resulting suspension was filtered over a membrane filter, the pH of the resulting solution was measured and the solubility was determined by HPLC. Solid material retained on the filter was analyzed by XRPD and TGA.

| analytical method | results | Comments |
| --- | --- | --- |
| solubility | >8.8 mg/100 ml | Saturated solution in water |
| pH | ~2.4 | |
| XRPD (solid residue) | crystalline | Almost identical; slight widening of the crystal lattice (?) |
| TGA (solid residue) | 13.9% up to 200° C.; 2.4% above 200° C. | |

Additional Solubility Data:

The dihydrochloride of formula (II) was stirred in 20 mL of different solvents for 20 h at 25° C. In all hydrous solvents approx. 2 g of the dihydrochloride of formula (II) have been solved completely.

| Solvent | Solubility |
| --- | --- |
| Acetone | 0.3 mg/100 ml practically insoluble |
| Acetonitrile | 1.1 mg/100 ml practically insoluble |
| Ethanol | 24.8 mg/100 ml very slightly soluble |
| PEG400 | 301 mg/100 ml slightly soluble |
| 0.1M HCl | ≥8800 mg/100 ml soluble |
| Buffer pH 4.5 | ≥8900 mg/100 ml soluble |
| Buffer pH 7.0 | ≥8700 mg/100 ml soluble |
| Water | ≥9400 mg/100 ml soluble |

Stability in Solution:

Hydrolytic Stability

The different aqueous solutions (0.05% of free base of formula (I); after addition of 50% 2-Propanol, [buffer solution filtered with 0.5 µm membrane filter]) were stored at 25° C. and 70° C. for 24 h and one week.

| Conditions | Appearance | Organic impurities, sum of all [Area %] | Organic impurities, single [Area %] |
| --- | --- | --- | --- |
| Water: | | | |
| Initial | slightly colored solution | 2.79 | 0.25 |
| 24 h, 25° C. | slightly colored solution | 3.43 | 0.23 |
| 24 h, 70° C. | slightly colored solution | 58.00 | 25.89 |
| 1 week, 25° C. | slightly colored solution | 5.33 | 0.54 |
| 1 week, 70° C. | slightly colored solution | 98.59 | 45.44 |

|  | | Organic impurities, sum of all | Organic impurities, single |
|---|---|---|---|
| Conditions | Appearance | [Area %] | [Area %] |
| Buffer pH 7: | | | |
| Initial | slightly colored turbid solution | 3.15 | 0.23 |
| 24 h, 25° C. | slightly colored turbid solution | 3.22 | 0.20 |
| 24 h, 70° C. | slightly colored solution | 56.06 | 23.25 |
| 1 week, 25° C. | slightly colored turbid solution | 4.85 | 0.82 |
| 1 week, 70° C. | slightly colored solution | 97.65 | 39.01 |
| 0.1M HCl: | | | |
| Initial | slightly colored solution | 5.87 | 1.13 |
| 24 h, 25° C. | slightly colored solution | 8.75 | 1.90 |
| 24 h, 70° C. | slightly colored solution | 92.49 | 22.82 |
| 1 week, 25° C. | slightly colored solution | 24.27 | 7.15 |
| 1 week, 70° C. | slightly colored solution | 100.00 | 25.48 |
| 0.1M NaOH: | | | |
| Initial | slightly colored solution | 30.72 | 6.51 |
| 24 h, 25° C. | slightly colored solution | 45.40 | 10.02 |
| 24 h, 70° C. | slightly colored solution | 99.88 | 23.94 |
| 1 week, 25° C. | slightly colored solution | 86.64 | 22.03 |
| 1 week, 70° C. | slightly colored solution | 99.90 | 32.63 |

IR and Raman Spectroscopy

| Apparatus and measuring conditions | |
|---|---|
| FT-IR/FT-Raman-Spectrometer | Bruker IFS 66v/Bruker RFS 100 |
| Spectral resolution | 2 cm$^{-1}$/2 cm$^{-1}$ |
| Number of interferograms | 32/64 |
| Wave number range | 4000-500 cm$^{-1}$/3500-100 cm$^{-1}$ |
| Laser power | —/350 mW |
| Sample preparation | KBr pellet/solid in test tube |

Assignment of the Characteristic Bands

TABLE

Assignment of the characteristic active vibrations to the spectrum with $\nu$ = stretching vibrations; $\delta$ = bending vibrations; o.o.p. = out of plane.";

| Assigned Structure | IR Band position [cm$^{-1}$] | Raman Band position [cm$^{-1}$] |
|---|---|---|
| $\nu$ N—H | 3336 | — |
| $\nu$ =C—H | 3176 | 3090 |
| $\nu$ C—H | 2942 | 2990-2963 |
| $\nu$ NH$^+$ | 2687-2474 | — |
| $\nu$ Amide I | 1669 | 1664 |
| $\nu$ C=C, $\nu$ C=N, $\delta$ N—H, Amide II | 1618-1477 | 1619-1476 |
| $\nu$ C—O | 1285 | 1291 |
| $\delta$ =C—H o.o.p. | 812 | — |

Figure 2:
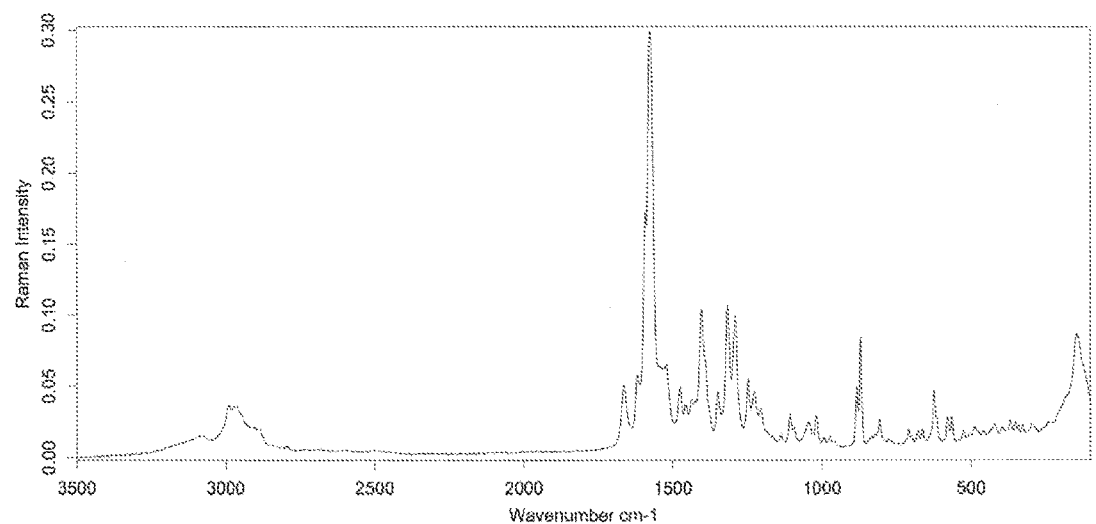
FIG. 2 shows a Raman spectrum of the dihydrochloride of formula (II).

$\nu$ = stretching vibrations;
$\delta$ = bending vibrations;
o.o.p. = out of plane The IR spectrum is given in FIG. 1.
The Raman spectrum is given in FIG. 2.

UV/VIS Spectroscopy

| Apparatus and measuring conditions | |
|---|---|
| UV/VIS spectrometer | Varian Cary 4 |
| Cuvette | Quartz, 1 cm |
| Wave number range | 200-800 nm |
| Sample preparation | 4.67 mg/500 mL water |
| Bands | 309 nm |

Figure 3:
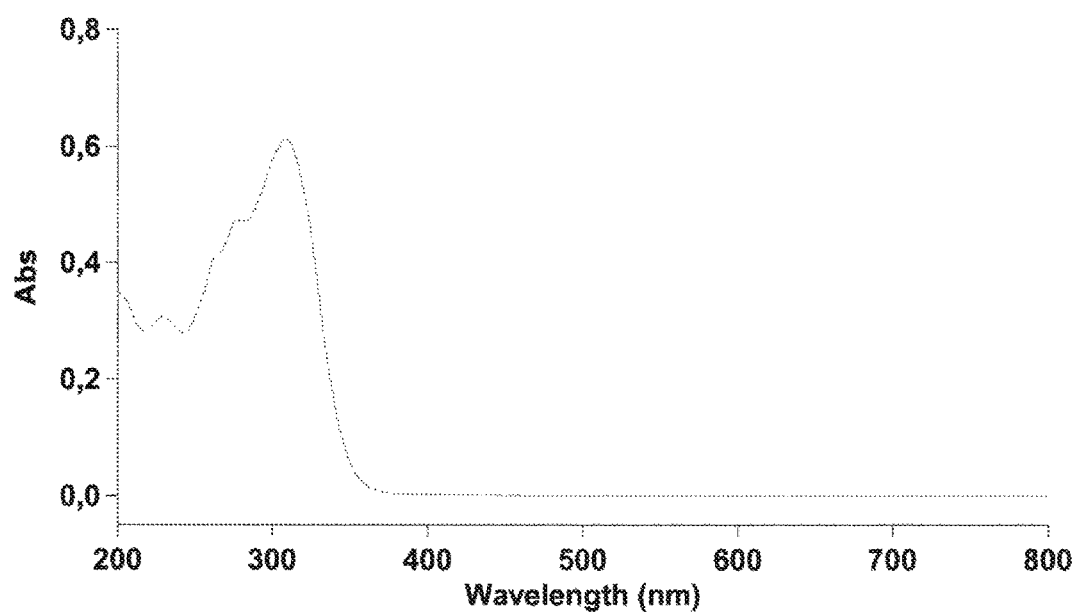
FIG. 3 shows a UV/VIS spectrum of the dihydrochloride of formula (II).

The UV/vis spectrum is given in FIG. 3.

NMR Spectroscopy $^1$H-NMR-Spectroscopy

Equipment and Experimental Parameters:

| | |
|---|---|
| NMR spectrometer | Bruker, model Avance |
| Working frequency | 500.13 MHz |
| Solvent | Dimethylsulfoxide (DMSO-d$_6$) |
| Internal reference compound | Tetramethylsilane (TMS) |
| Concentration | 3.08 mg/mL solution |
| Diameter of sample tube | 5 mm |
| Temperature | approx. 25° C. |
| Technique | Fourier transform mode |
| Spectral width | 20.65 ppm |
| Digital resolution | 0.079 Hz/Pt |
| Pulse length | 4.5 µsec, 30° Pulse flip angle |
| Acquisition time | 6.34 sec |
| Relaxation time | 0.5 sec |
| No. of free induction decays | 32 |

Structural Formula for the Assignment of NMR Signals

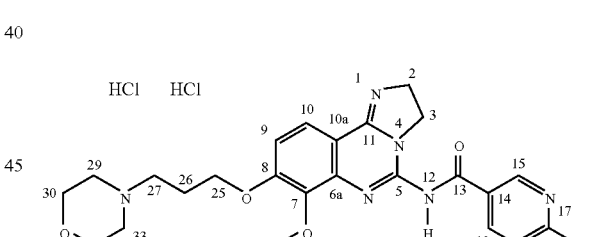

Chemical Shift, Signal Multiplicity, Relative Number of Nuclei:

| H-atoms(a) | Chemical shift $\delta$ (ppm) | Multiplicity and coupling constants (b) | no. of nuclei H/molecule |
|---|---|---|---|
| H-26 | 2.32 | M | 2 |
| H-29; H-33 | 3.11; 3.48 | M; M | 2; 2 |
| H-30; H-32 | 3.83; 3.98 | M; M | 2; 2 |
| H-27 | 3.29 | M | 2 |
| —OCH$_3$ | 4.00 | S | 3 |
| H-25 | 4.37 | T | 2 |
| H-2; H-3 | 4.47; 4.19 | T; T | 2; 2 |
| H-9 | 7.39 | D | 1 |
| NH$_2$ | 7.54 | S | 2 |
| H-10 | 8.21 | D | 1 |

| H-atoms(a) | Chemical shift δ (ppm) | Multiplicity and coupling constants (b) | no. of nuclei H/molecule |
|---|---|---|---|
| H-16; H-20 | 8.97 | S | 1; 1 |
| HCl | 11.1; 12.6 | bS; bS | 1; 1 |
| H-12 | 13.4 | bS | 1 |

Figure 4:
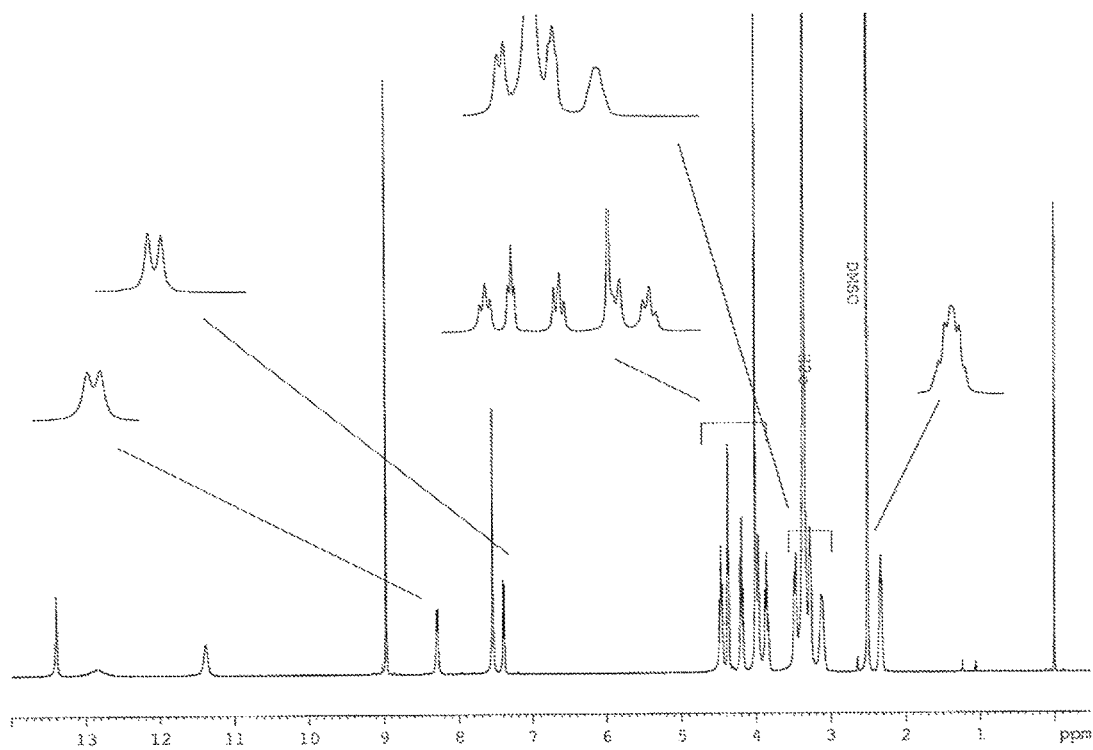
FIG. 4 shows a $^1$H-NMR spectrum of the dihydrochloride of formula (II).

(a) Numbering refers to the structural formula for the assignment of NMR-signals.
(b) S = Singlet bS = broad Singlet D = Doublet T = Triplet M = Multiplet The $^1$H-NMR Spectrum of the dihydrochloride of formula (II) is given in FIG. 4.

$^{13}$C-NMR-Spectroscopy

| Equipment and experimental parameters | |
|---|---|
| NMR spectrometer | Bruker, model Avance |
| Working frequency | 125.76 MHz |
| Solvent | Dimethylsulfoxide-d$_6$ (DMSO) |
| Internal reference compound | Tetramethylsilane (TMS) |
| Concentration | 37.2 mg/mL solution |
| Diameter of sample tube | 5 mm |
| Temperature | approx. 27° C. |
| Technique | Fourier transform mode |
| Spectral width | 240.95 ppm |
| Digital resolution | 0.4624 Hz/Pt |
| Pulse length | 11.0 μsec, 90° Pulse flip angle |
| Acquisition time | 1.08 sec |
| Relaxation time | 4 sec |
| No. of free induction decays | 256 |

Chemical Shift, Signal Multiplicity, Rel. No. of Nuclei:

| C-atoms(a) | Chemical shift δ (ppm) | Multiplicity and coupling constants (b) | no. of nuclei C/molecule |
|---|---|---|---|
| C-26 | 22.73 | T | 1 |
| C-2; C-3 | 44.96; 45.65 | T; T | 1; 1 |
| C-29; C-33 | 50.84 | T | 1; 1 |
| C-27 | 53.01 | T | 1 |
| OCH$_3$ | 61.24 | Q | 1 |
| C-30; C-32 | 63.03 | T | 1; 1 |
| C-25 | 66.81 | T | 1 |
| C-10a | 100.79 | S | 1 |
| C-9 | 112.17 | D | 1 |
| C-15 | 118.16 | S | 1 |
| C-10 | 123.86 | D | 1 |
| C-6a | 132.43 | S | 1 |
| C-7 | 133.95 | S | 1 |
| C-5 | 148.58 | S | 1 |
| C-11 | 156.29 | S | 1 |
| C-8 | 156.89 | S | 1 |
| C-16; C-20 | 160.20 | D | 1; 1 |
| C-18 | 164.61 | S | 1 |
| C=O | 175.65 | S | 1 |

(a) Numbering refers to the structural formula for the assignment of NMR-signals.
(b) S = Single (C) D = Doublet (CH) T = Triplet (CH$_2$) Q = Quadruplet (CH$_3$)

Figure 5:
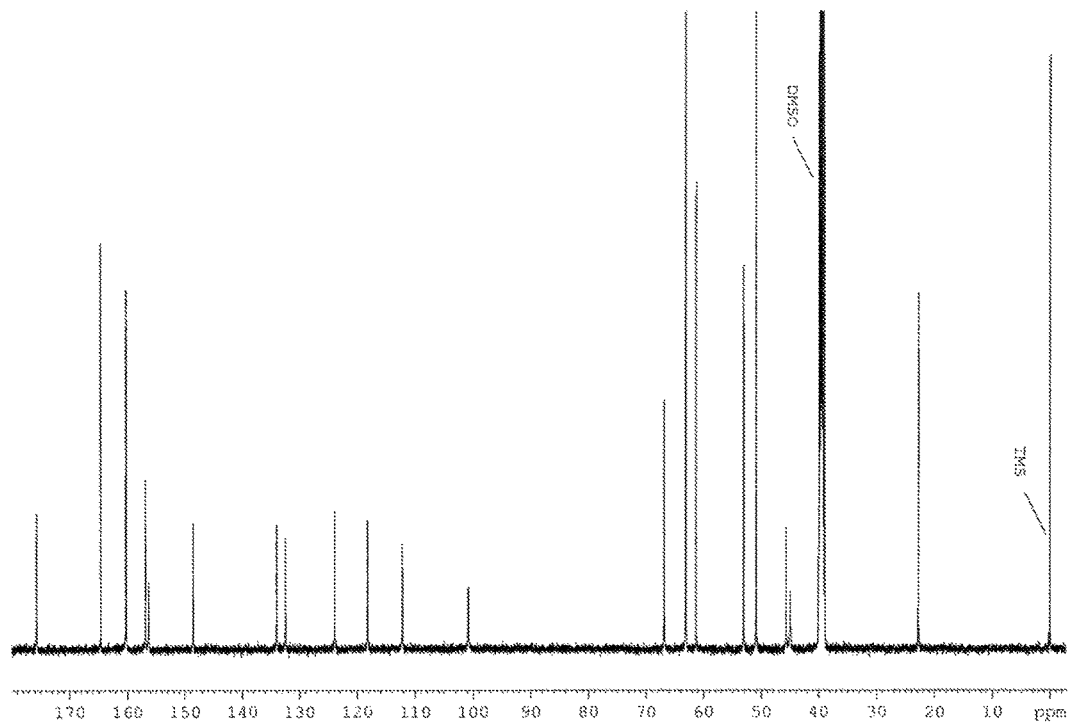
FIG. 5 shows a $^{13}$C-NMR spectrum of the dihydrochloride of formula (II).
Figure 6:
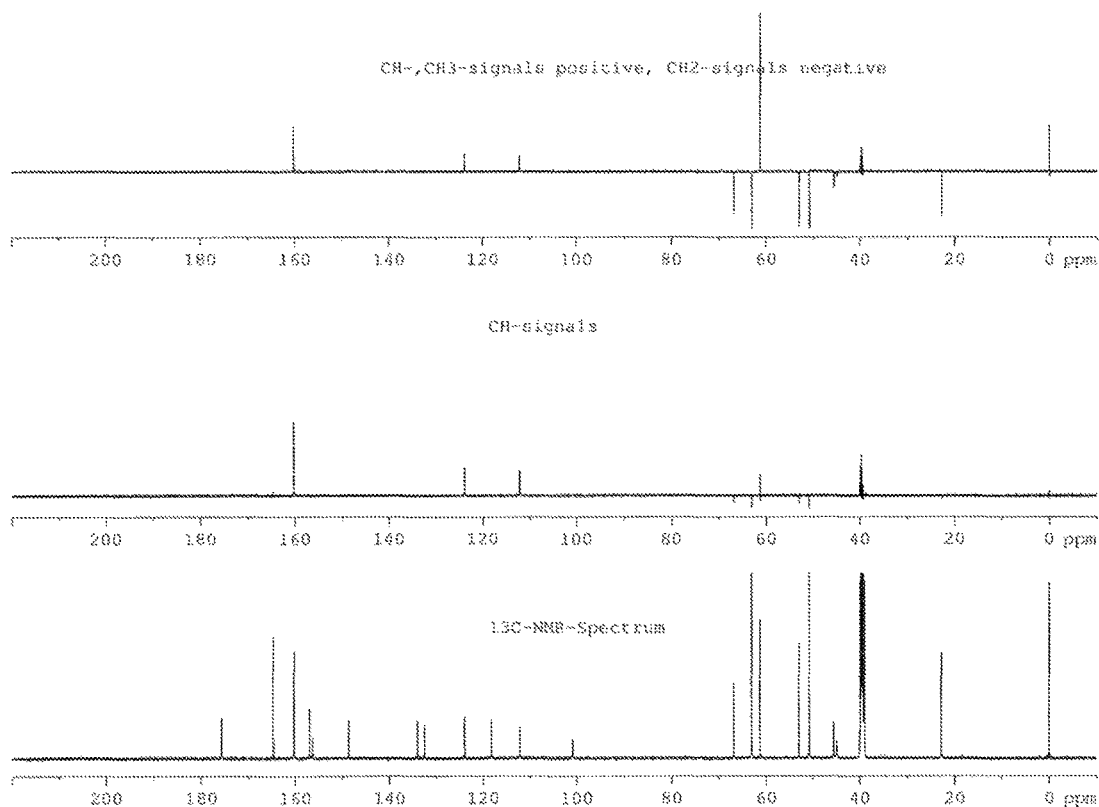
FIG. 6 shows another $^{13}$C-NMR spectrum of the dihydrochloride of formula (II).

The $^{13}$C-NMR Spectra of the dihydrochloride of formula (II) are given in FIGS. 5 and 6.

Mass Spectrometry

| Instrumental Parameters | |
|---|---|
| Mass spectrometer | Waters ZQ |
| Ionization mode | ESI (Electrospray-Ionization) |
| Solvent | CH$_3$CN/H$_2$O |

| Interpretation of the Spectrum | | |
|---|---|---|
| Mass value (m/z) | Rel. Intensity (%) | Ion Formation |
| 481.2 | 46 | (M + H)$^+$ |
| 354.1 | 5 | (C16H16N7O3)$^+$ |
| 261.7 | 26 | (M + 2H + CH$_3$CN)$^{+2}$ |
| 241.2 | 100 | (M + 2H)$^{+2}$ |

Figure 7:
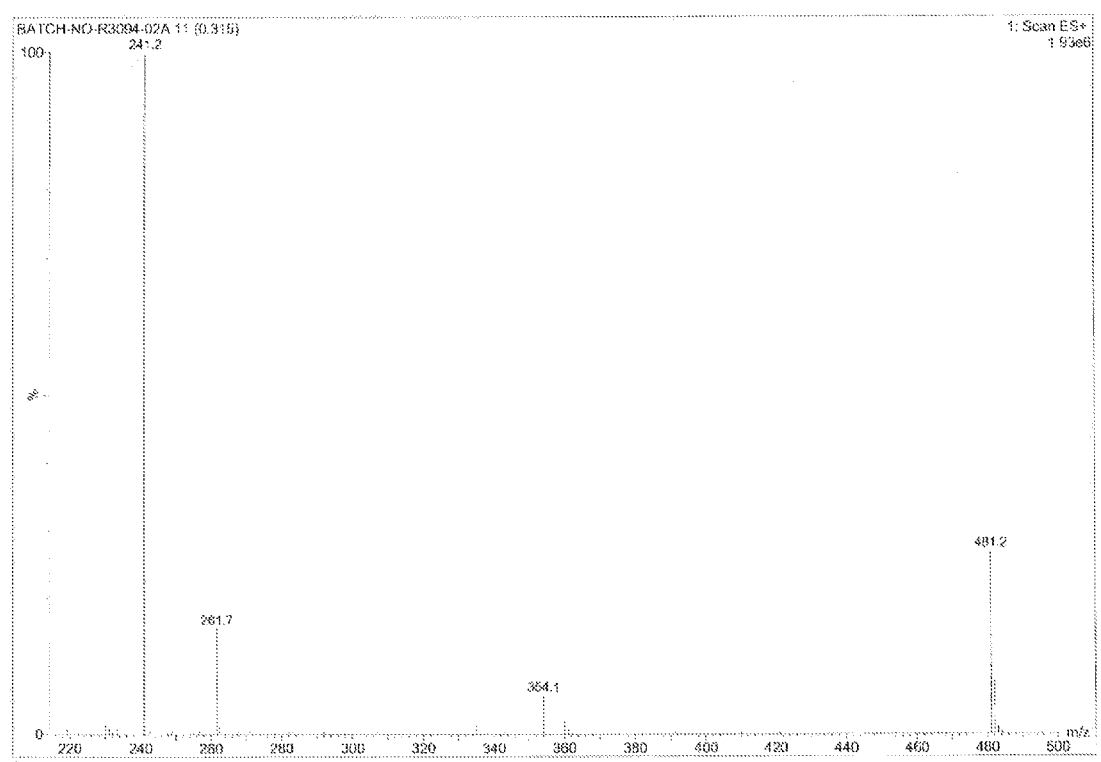
FIG. 7 shows a mass spectrum of the dihydrochloride of formula (II).

The Mass Spectrum of the dihydrochloride of formula (II) is given in FIG. 7. Refer to the spectrum for relative peak intensities.

Elemental Analysis

Elemental analysis was conducted by Bayer Industry Services, Leverkusen, Germany.

Results

| Element | Measured [%] | Calculated [%] | Calculated including 7.0% water [%] | Difference |
|---|---|---|---|---|
| C | 47.5 | 49.9 | 46.4 | 1.1 |
| H | 5.7 | 5.5 | 5.9 | 0.2 |
| N | 19.1 | 20.3 | 18.8 | 0.3 |
| O | 18.1 | 11.6 | 17.0 | 1.1 |
| Cl | 11.9 | 12.8 | 11.9 | 0.0 |
| Sum | 102.3 | 100.1 | 100.0 | — |

The elemental analysis is consistent with a dihydrochloride salt of formula II with 7% water.

Example 2: Further Method of Preparation of the Dihydrochloride Salt of Formula (II)

To a suspension of 366 g of compound of formula (I) in 1015 g water, 183 g of an aqueous hydrochloric acid solution (32%) were added while maintaining the temperature at 20° C. (+−2°) until a pH of 3 to 4 was reached. The resulting mixture was stirred at room temperature for more than 10 min. filtered and the filtercake washed with additional 82 g of water. The filtrate was adjusted to pH 1.8 to 2.0 using aqueous hydrochloric acid solution (32%). The mixture was stirred for 10 min. at room temperature, 146 g of ethanol (100%) were added and stirred for another 10 min. 1 g of seed crystals were added, followed by 1592 g ethanol within 5 h. The resulting substance was removed by filtration, washed with a water-ethanol mixture and dried in vacuo to give 410 g (97%) of the dihydrochloride of formula (II) of a purity >99% according to HPLC.

Comparative Example 1: Monohydrochloride of Compound of Formula (I)

To a suspension of the compound of formula (I) (0.5 g, 1.04 mmol) in an acetone/water mixture (9 mL, 8:2 v/v) was added a concentrated hydrochloric acid solution (89 μL, 1.07 mmol, 1.0 equiv, 36% HCl). A visible change in the mixture was observed, but a clear solution was not obtained. The mixture was heated with stirring at 50° C. for 0.5 h, followed by 35° C. for 3 days, then room temperature for 2 h. The remaining suspended solids were removed by filtration, washed acetone/water, (8:2 v/v), and dried (40° C., 100 mbar, 16 h) to give the desired product (0.5 g).

Characterization:

| analytical method | results | Comments |
|---|---|---|
| HPLC, wt % DS | ~85.8 wt %, ~98.4% area %, sum of impurities ~1.6% | Quality significantly improved with regard to Batch A |
| IC, wt % salt former | 6.0 wt % | ~1:1-salt |
| TGA | 6.3% till 200° C. | |
| DSC | broad peak at 75° C. | |
| XRPD | Predominantly amorphous | |
| Microscopy | n.t. | |

Results indicate that a crystalline monohydrochloride was not formed. Though the purity of the base was improved by the experiment, no further studies were performed, as the material was predominantly amorphous.

Comparative Example 2: Bis (Hydrogen Sulfate) Salt of the Compound of Formula (I)

To a suspension of the compound of formula (I) (0.5 g, 0.103 mmol) in an acetone/water mixture (9 mL, 9:1 v/v) was added a concentrated sulfuric acid solution (213 mg, 96% H2SO4, 2 equiv.). A visible change in the mixture was observed, but a clear solution was not obtained. The mixture was heated with stirring at 50° C. for 0.5 h, followed by 35° C. for 3 days, then room temperature for 2 h. The remaining suspended solids were isolated by filtration, washed (acetone/water, 9:1 v/v), and dried (40° C., 100 mbar, 16 h) to give approximately 30 mg of the desired product.

Comparative Example 3: Citric Acid Salt of the Compound of Formula (I)

To a suspension of the compound of formula (I) (3.0 g, 6.24 mmol) in an ethanol/water mixture (50 mL, 1:2 v/v) was added citric acid (2.4 g, 10.2 mmol, 1.6 equiv). The mixture was heated with stirring to 35° C., 25 ml water and 100 ml ethanol were added and stirring was continued at 35° C. for 2 h. The resulting clear solution was cooled to room temperature and stirring was continued for 3 days. The resulting solids were isolated by filtration, washed with 10 ml ethanol, and dried (40° C., 100 mbar, 24 h) to give the desired product (3.8 g, 90% yield). Note: filtration of this material was very slow.

Characterization:

| analytical method | results | Comments |
|---|---|---|
| HPLC, wt % DS | 64.1 wt %, 98.1 area %, sum of impurities 1.9% | |
| IC, wt % salt former | 30.2 wt % | >1:1-salt |
| TGA | 3.8% wt % till 50° C.; 29.4% at 130 to 200° C. | |
| DSC | Broad peaks | melts with decomposition |
| XRPD | Crystalline | significant amounts of free base detectable |
| Microscopy | Microcrystalline; agglomerates | |

All results indicate that a uniform, real salt was not formed but rather a mixture of the a citric salt, free base and/or citric acid.

Stability as Solid:

The citric acid salt of compound of formula (I) (100 mg from Comparative Example 3) was stored at 90° C. for 1 week.

| analytical method | results | Comments |
|---|---|---|
| HPLC, wt % DS | 62.7 wt % | |
| HPLC, area % DS | 96.3% | Slightly unstable; Sum of impurities slightly higher (3.7% vs. 1.9%) |

Aqueous Solubility:

The citric acid salt of the compound of formula (I) (500 mg from Comparative Example 3) was stirred at 25° C. for 20 h in water (5 mL). The resulting suspension was filtered over a membrane filter, the pH of the solution was measured and solubility was determined by HPLC. The solid material retained on the filter was analyzed by XRPD and TGA.

| analytical method | results | Comments |
|---|---|---|
| solubility | ~8.5 mg/100 ml | |
| pH | 3.9 | Saturated solution in water |
| XRPD (solid residue) | Broad signals | Significant change; less crystalline |
| TGA (solid residue) | 4.4% at 30° to120° C.; 27% at 120° to 250° C. | |

Comparative Example 4: Succinic Acid Salt of the Compound of Formula (I)

To a suspension of the compound of formula (I) (3.0 g, 6.24 mmol) in an acetone/water mixture (50 mL, 8:2 v/v) was added succinic acid (1.48 g, 12.5 mmol, 2 equiv) to form a white suspension. The mixture was heated with stirring at 50° C. for 0.5 h, followed by 35° C. for 3 days, then room temperature for 2 h. The appearance of the mixture did not change significantly over this period. The resulting solids were removed by filtration, washed with few mls of an acetone/water mixture (8:2 v/v), and dried (40° C., 100 mbar, 16 h) to give the desired product (3.4 g, 91%).

Characterization:

| analytical method | results | Comments |
|---|---|---|
| HPLC, wt % DS | 75.6 wt %, ~97.6% area %, sum of impurities ~2.4% | |
| IC, wt % salt former | 15.1 wt % | <1:1-salt |
| TGA | 3.2% up to 50° C.; 17.6% @ 140-220° C. | Similar to free base |
| DSC | Broad peaks | Similar to free base |
| XRPD | predom. crystalline | significant amounts of free base detectable |
| Microscopy | agglomerates | |

The characterization suggests that a uniform, stoichiometric salt was not formed but rather a mixture of a succinate and the free base.

Stability as Solid:

The succinic acid salt of the compound of formula (I) (100 mg from Comparative Example 4) was stored at 90° C. for 1 week.

| analytical method | results | Comments |
|---|---|---|
| HPLC, wt % DS | 48.4 wt % | brownish solid after 1 w 90° C. |
| HPLC, area % DS | ~97.6% (sum of impurities ~2.4%) | not stable |

Aqueous Solubility:

The succinic acid salt of the compound of formula (I) (500 mg from Comparative Example 4) was stirred in water (5 mL) at 25° C. for 20 h. The resulting suspension was filtered over a membrane filter, the pH of the solution was measured, and the solubility was determined by HPLC. The solid material retained on the filter was analyzed by XRPD and TGA.

| analytical method | results | Comments |
|---|---|---|
| solubility | ~5.5 mg/100 ml | |
| pH | 4.7 | Saturated solution in water |
| XRPD (solid residue) | Partly crystalline | Significant change; partly amorphous; free base detectable |
| TGA (solid residue) | 5.5% at 30° to 120° C.; 15% at 120° to 240° C. | |

Comparative Example 5: Maleic Acid Salt of the Compound of Formula (I)

To a suspension of the compound of formula (I) (3.0 g, 6.24 mmol) in an acetone/water mixture (50 mL, 8:2 v/v) was added maleic acid (1.45 g, 12.5 mmol, 2.0 equiv) to form an almost clear solution that became a suspension after 5 min. The mixture was heated with stirring at 50° C. for 0.5 h, followed by 35° C. for 3 days, then room temperature for 2 h. The resulting solids were isolated by filtration, washed with an acetone/water mixture (8:2 v/v), and dried (40° C., 100 mbar, 16 h) to give the desired product (4.0 g, 90%). Note: filtration of this material proceeded well.
Characterization:

| analytical method | results | Comments |
|---|---|---|
| HPLC, wt % DS | 62.7 wt %, ~95.2% area %, sum of impurities ~4.8% | |
| IC, wt % salt former | 30.7 wt % | ~1:2-salt |
| TGA | 5.8% till 50° C.; 3.7% @ 80-150° C.; 20.7% @ 160-210° C. | |
| DSC | broad peaks | |
| XRPD | crystalline | differences prob. due to solvent integration; no free base detectable |
| Microscopy | crystals | |

Results indicate that a crystalline dimaleate was formed. The purity of the base was not improved by the formation of the salt in this case.
Stability as Solid:

The maleic acid salt of the compound of formula (I) (100 mg from Comparative Example 5) was stored at 90° C. for 1 week.

| analytical method | results | Comments |
|---|---|---|
| HPLC, wt % DS | 59.4 wt % | |
| HPLC, area % DS | ~96.9% (sum of impurities ~3.1%) | Stable |

Aqueous Solubility:

The maleic acid salt of the compound of formula (I) (500 mg from Comparative Example 5) was stirred in water (5 mL) at 25° C. for 20 h. The resulting suspension was filtered over a membrane filter, the pH of the solution was measured, and the solubility was determined by HPLC. The solid material retained on the filter was analyzed by XRPD and TGA.

| analytical method | results | Comments |
|---|---|---|
| solubility | >8.1 mg/100 ml | |
| pH | 3.1 | Saturated solution in water |
| XRPD (solid residue) | crystalline | Almost identical; slight widening of the crystal lattice (?) |
| TGA (solid residue) | 8% at 30°-90° C.; 2.5% at 100°-150° C.; 14% above 150° C. | |

Comparative Example 6: Methanesulphonic Acid Salt of the Compound of Formula (I)

To a suspension of the compound of formula (I) (3.0 g, 6.24 mmol) in an acetone/water mixture (50 mL, 9:1 v/v) was added methanesulphonic acid (1.2 g, 12.5 mmol, 2 equiv) to form a sticky material. The mixture was heated with stirring at 50° C. for 0.5 h, followed by 35° C. for 3 days. The appearance of the mixture did not change significantly over this period. Additional acetone (50 mL) was added to the mixture and stirring was continued at room temperature for an additional 5 days, yielding a filterable suspension along with sticky material. The suspension was removed by filtration, washed with acetone and dried (40° C., 100 mbar, 16 h) to give the desired product (3.5 g, 83.3%).
Characterization:

| analytical method | results | Comments |
|---|---|---|
| HPLC, wt % DS | 62.9 wt %, ~96.1% area %, sum of impurities ~3.9% | |
| IC, wt % salt former | 26.4 wt % | ~1:2-salt |
| TGA | 6.3% @ 30-100° C.; 22% @ 220° C. (decomp.) | |
| DSC | Broad peaks | |
| XRPD | predom. crystalline | partly amorphous |
| Microscopy | Microcryst., agglomerates | |

All results indicate that a crystalline dimesylate salt can be formed. Obviously, optimal crystallization conditions have not been found and/or the dimesylate is very sensitive to its formation conditions as the material was amorphous in part. The polymorphic form produced so far seems to be able to take up solvents/water.
Stability as Solid:

The methanesulphonic acid salt of the compound of formula (I) (100 mg from Comparative Example 6) was stored at 90° C. for 1 week.

| analytical method | results | Comments |
|---|---|---|
| HPLC, wt % DS | 59.5 wt % | |
| HPLC, area % DS | ~96.7% (sum of impurities ~3.3%) | Stable |

Aqueous Solubility:

The methanesulphonic acid salt of the compound of formula (I) (500 mg from Comparative Example 6) was stirred at 25° C. for 20 h in water (5 mL). The sample was almost completely dissolved, The resulting mixture was filtered over a membrane filter, the pH of the solution was measured, and the solubility was determined by HPLC. However, not enough solid material was left after filtration for further analysis.

| analytical method | results | Comments |
|---|---|---|
| solubility | >8.3 mg/100 ml | |
| pH | ~2.3 | Saturated solution in water |
| XRPD (solid residue) | n.t. | |
| TGA (solid residue) | n.t. | |

CONCLUSIONS

From a physicochemical point of view, the dihydrochloride salt of formula (II) (Example 4) of the present invention provides surprising technical results as seen in the Examples and Comparative Examples, supra, as summarised in Table 5, infra:

TABLE 5

| Property | Citric acid (Comp. Ex. 3) | Succinic acid (Comp. Ex. 4) | Maleic acid (Comp. Ex. 5) | Me-sulfonic acid (Comp. Ex. 6) | Hydrochloric acid (Ex. 1) | Compound of formula (I) (free base) | Criteria |
|---|---|---|---|---|---|---|---|
| stoichiometry | ~1:1 | ~1:1 | ~1:2 | ~1:2 | 1:2 | | Based on HPLC/IC |
| chem. process | ○ | – | ○ | – | ○ | – | yield, final processing |
| purity | + | + | ○ | ○ | + | ○ | area % HPLC |
| salt stability | ○ | – | + | n.d. | ++ | n.a. | disintegration with/in water |
| crystallinity | ○ | – | + | ○ | ++ | ○ | XRPD |
| hydrates | | | | | ~4 H$_2$O | | 1 w @ 95% r.h.; aqu. solub. |
| aqu. solubility | ~8.5 | ~5.5 | >8.1 | >8.3 | >8.8 | – | 16 h @ 25° C. (mg/100 ml) |
| therm. stab. solution | n.d. | n.d. | n.d. | n.d. | n.d. | ○ | 24 h @ 70° C. 1 w @ 25° C. |
| therm. stab. solid | + | –– | + | + | + | ++ | 1 w @ 90° C. |
| Overall CD | ○ | –– | ○ | –– | + | ○ | |

--- very disadvantageous
– disadvantageous
○: indifferent
+: advantageous
++: very advantageous
n.a.: not applicable
n.f.: not found
n.d.: not determined; no clear solution after filtration, probably due to formation of micelles.

First, as seen from Comparative Example 1, unexpectedly, results indicate that a crystalline monohydrochloride of the compound of formula (I) was not formed: it was predominantly amorphous. In contrast, as seen from Example 1, the dihydrochloride salt of formula (II) can form a crystalline, stable dihydrochloride salt. The crystalline dihydrochloride salt is stable against reversion in water to the free base.

Further, the dihydrochloride salt of the present invention has a superior stability in water compared to the other salts mentioned. This means that the salt does not revert in water to the free base under the conditions tested, i.e. precipitation of the free base does not occur.

Crystallinity of the dihydrochloride salt of the present invention was superior vs. the monohydrochloride salt (which was found predominantly amorphous in XRPD).

Secondly, as seen from Comparative Example 5, (characterisation table), from the XRPD results, the comments are that there are differences in the maleate salt of the compound of formula (I) of Comparative Example 5: as is mentioned, these differences are probably due to solvent integration.

Further, it can be seen from Comparative Example 5 that the purity of the base was not improved by the formation of the maleate salt. In contrast, as seen in Example 1 (the dihydrochloride salt of the present invention), it can be seen that the purity of the free base was improved by the formation of the dihydrochloride salt.

Further, the quality of the drug substance is improved upon dihydrochloride salt formation.

Moreover, an additional technically advantageous property of the dihydrochloride salt (II) of the present invention is that the crystalline salt form ideally would furthermore help to improve the purification process and the final processing: it is stable as a solid and in solution, and fits into the galenic strategy (e.g. the salt of the present invention dissolves more rapidly than the compound of formula (I) (the free base), which represents a clear technical advantage.

Overall therefore, as seen from Table 5, vide supra, the dihydrochloride is surprisingly advantageous in terms of purity, salt stability, crystallinity, and aqueous solubility.

Moreover, very importantly, as seen in the PI3Kα and PI3Kβ biochemical assays: both the free base and the dihydrochloride salt showed similar activities in both PI3Kα and PI3Kβ biochemical assays. Slightly better potency with the dihydrochloride salt form might be due to improved solubility. This is clearly very advantageous.

Pharmaceutical Formulations of the Salt of the Present Invention

As mentioned above, the salt of the present invention may be in the form of a pharmaceutical formulation which is ready for use to be administered simultaneously, concurrently, separately or sequentially. The components may be administered independently of one another by the oral, intravenous, topical, local installations, intraperitoneal or nasal route.

Said compositions can be utilized to achieve the desired pharmacological effect by administration to a patient in need thereof. A patient, for the purpose of this invention, is a mammal, including a human, in need of treatment for the particular condition or disease. Therefore, the present invention includes the salt of the present invention which is in the form of a pharmaceutical formulation composition that is comprised of a pharmaceutically acceptable carrier and a pharmaceutically effective amount of a said salt. A pharmaceutically acceptable carrier is preferably a carrier that is relatively non-toxic and innocuous to a patient at concentrations consistent with effective activity of the active ingredient so that any side effects ascribable to the carrier do not vitiate the beneficial effects of component, and/or combination. A pharmaceutically effective amount of a combination is preferably that amount which produces a result or exerts an influence on the particular condition being treated. The salts of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

For oral administration, the salts can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard-or soft-shelled gelatin type containing, for example, surfactants, lubricants, and inert fillers such as lactose, sucrose, calcium phosphate, and corn starch.

In another embodiment, the salt of this invention may be tableted with conventional tablet bases such as lactose, sucrose and cornstarch in combination with binders such as acacia, corn starch or gelatin, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, coloring agents, and flavoring agents such as peppermint, oil of wintergreen, or cherry flavoring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavoring and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavoring and coloring agents.

The salt of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono-or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, issued Jun. 11, 1991, incorporated herein by reference). Such patches may be constructed for continuous, pulsatile, or on demand delivery of pharmaceutical agents.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized. Such ingredients and procedures include those described in the following references, each of which is incorporated herein by reference: Powell, M. F. et al, "Compendium of Excipients for Parenteral Formulations" *PDA Journal of Pharmaceutical Science & Technology* 1998, 52(5), 238-311; Strickley, R. G "Parenteral Formulations of Small Molecule Therapeutics Marketed in the United States (1999)-Part-1" *PDA Journal of Pharmaceutical Science Et Technology* 1999, 53(6), 324-349; and Nema, S. et al, "Excipients and Their Use in Injectable Products" *PDA Journal of Pharmaceutical Science & Technology* 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal);

aerosol propellants (examples include but are not limited to carbon dioxide, $CCl_2F_2$, $F_2ClC-CClF_2$ and $CClF_3$)

air displacement agents (examples include but are not limited to nitrogen and argon);

antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate)

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection)

chelating agents (examples include but are not limited to edetate disodium and edetic acid)

colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate)

flavorants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin);

oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono-or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas)

plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, cross-linked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide);

tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile IV Solution: A 5 mg/mL solution of the desired compound of this invention can be made using sterile, injectable water, and the pH is adjusted if necessary. The solution is diluted for administration to 1-2 mg/mL with sterile 5% dextrose and is administered as an IV infusion over about 60 minutes.

Lyophilized Powder for IV Administration: A sterile preparation can be prepared with (i) 100-1000 mg of the desired compound of this invention as a lypholized powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular Suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Method of Treating Cancer

Within the context of the present invention, the term "cancer" includes, but is not limited to, cancers of the breast, lung, brain, reproductive organs, digestive tract, urinary tract, liver, eye, skin, head and neck, thyroid, parathyroid and their distant metastases. Those disorders also include multiple myeloma, lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small-intestine, and salivary gland cancers.

Tumors of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

The present invention relates to a method for using the salt of the present invention, to treat cancer, as described infra, particularly mammalian NSCLC, CRC, melanoma, pancreatic cancer, hepatocyte or breast cancer. The salt of the present invention can be utilized to inhibit, block, reduce, decrease, etc., cell proliferation and/or cell division, and/or produce apoptosis, in the treatment or prophylaxis of cancer, in particular NSCLC, CRC, melanoma, pancreatic cancer, hepatocyte carcinoma or breast cancer. This method comprises administering to a mammal in need thereof, including a human, an amount of a combination of this invention, or a pharmaceutically acceptable salt, isomer, polymorph, metabolite, hydrate, solvate or ester thereof; etc. which is effective for the treatment or prophylaxis of cancer, in particular NSCLC, CRC, melanoma, pancreatic cancer, hepatocyte carcinoma or breast cancer.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Dose and Administration

Based upon standard laboratory techniques known to evaluate compounds useful for the treatment or prophylaxis of cancer, in particular NSCLC, CRC, melanoma, pancreatic cancer, hepatocyte carcinoma or breast cancer, by standard toxicity tests and by standard pharmacological assays for the determination of treatment of the conditions identified above in mammals, and by comparison of these results with the results of known medicaments that are used to treat these conditions, the effective dosage of the salt of this invention can readily be determined for treatment of the indication. The amount of the active ingredient to be administered in the treatment of the condition can vary widely according to many considerations, including, but not limited to the particular combination and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1,500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

The specific initial and continuing dosage regimen for each patient will vary according to the nature and severity of the condition as determined by the attending diagnostician, the activity of the specific combination employed, the age and general condition of the patient, time of administration, route of administration, rate of excretion of the drug, drug salts, and the like. The desired mode of treatment and number of doses of a combination of the present invention or a pharmaceutically acceptable salt or ester or composition thereof can be ascertained by those skilled in the art using conventional treatment tests.

Therapies Using the Salt of the Present Invention: One or More Further Pharmaceutical Agents.

The salt of the present invention can be administered as the sole pharmaceutical agent or in combination with one or more further pharmaceutical agents where the resulting combination of the salt of the present invention and the further pharmaceutical agent causes no unacceptable adverse effects. For example, the salt of the present invention can be combined with a component C, i.e. one or more further pharmaceutical agents, such as known anti-angiogenesis, anti-hyper-proliferative, antiinflammatory, analgesic, immunoregulatory, diuretic, antiarrhythmic, anti-hypercholsterolemia, anti-dyslipidemia, anti-diabetic or antiviral agents, and the like, as well as with admixtures and salts thereof.

Component C, can be one or more pharmaceutical agents such as aldesleukin, alendronic acid, alfaferone, alitretinoin, allopurinol, aloprim, aloxi, altretamine, aminoglutethimide, amifostine, amrubicin, amsacrine, anastrozole, anzmet, aranesp, arglabin, arsenic trioxide, aromasin, 5-azacytidine, azathioprine, BCG or tice BCG, bestatin, betamethasone acetate, betamethasone sodium phosphate, bexarotene, bleomycin sulfate, broxuridine, bortezomib, busulfan, calcitonin, campath, capecitabine, carboplatin, casodex, cefesone, celmoleukin, cerubidine, chlorambucil, cisplatin, cladribine, cladribine, clodronic acid, cyclophosphamide, cytarabine, dacarbazine, dactinomycin, DaunoXome, decadron, decadron phosphate, delestrogen, denileukin diftitox, depo-medrol, deslorelin, dexomethasone, dexrazoxane, diethylstilbestrol, diflucan, docetaxel, doxifluridine, doxorubicin, dronabinol, DW-166HC, eligard, elitek, ellence, emend, epirubicin, epoetin alfa, epogen, eptaplatin, ergamisol, estrace, estradiol, estramustine phosphate sodium, ethinyl estradiol, ethyol, etidronic acid, etopophos, etoposide, fadrozole, farston, filgrastim, finasteride, fligrastim, floxuridine, fluconazole, fludarabine, 5-fluorodeoxyuridine monophosphate, 5-fluorouracil (5-FU), fluoxymesterone, flutamide, formestane, fosteabine, fotemustine, fulvestrant, gammagard, gemcitabine, gemtuzumab, gleevec, gliadel, goserelin, granisetron HCl, histrelin, hycamtin, hydrocortone, eyrthro-hydroxynonyladenine, hydroxyurea, ibritumomab tiuxetan, idarubicin, ifosfamide, interferon alpha, interferon-alpha 2, interferon alfa-2A, interferon alfa-2B, interferon alfa-n1, interferon alfa-n3, interferon beta, interferon gamma-1a, interleukin-2, intron A, iressa, irinotecan, kytril, lentinan sulphate, letrozole, leucovorin, leuprolide, leuprolide acetate, lenalidomide, levamisole, levofolinic acid calcium salt, levothroid, levoxyl, lomustine, lonidamine, marinol, mechlorethamine, mecobalamin, medroxyprogesterone acetate, megestrol acetate, melphalan, menest, 6-mercaptopurine, Mesna, methotrexate, metvix, miltefosine, minocycline, mitomycin C, mitotane, mitoxantrone, Modrenal, Myocet, nedaplatin, neulasta, neumega, neupogen, nilutamide, nolvadex, NSC-631570, OCT-43, octreotide, ondansetron HCl, orapred, oxaliplatin, paclitaxel (when component B is not itself paclitaxel), pediapred, pegaspargase, Pegasys, pentostatin, picibanil, pilocarpine HCl, pirarubicin, plicamycin, porfimer sodium, prednimustine, prednisolone, prednisone, premarin, procarbazine, procrit, raltitrexed, RDEA 119, rebif, rhenium-186 etidronate, rituximab, roferon-A, romurtide, salagen, sandostatin, sargramostim, semustine, sizofiran, sobuzoxane, solu-medrol, sparfosic acid, stem-cell therapy, streptozocin, strontium-89 chloride, synthroid, tamoxifen, tamsulosin, tasonermin, tastolactone, taxotere, teceleukin, temozolomide, teniposide, testosterone propionate, testred, thioguanine, thiotepa, thyrotropin, tiludronic acid, topotecan, toremifene, tositumomab, trastuzumab, treosulfan, tretinoin, trexall, trimethylmelamine, trimetrexate, triptorelin acetate, triptorelin pamoate, UFT, uridine, valrubicin, vesnarinone, vinblastine, vincristine, vindesine, vinorelbine, virulizin, zinecard, zinostatin stimalamer, zofran, ABI-007, acolbifene, actimmune, affinitak, aminopterin, arzoxifene, asoprisnil, atamestane, atrasentan, BAY 43-9006 (sorafenib), avastin, CCI-779, CDC-501, celebrex, cetuximab, crisnatol, cyproterone acetate, decitabine, DN-101, doxorubicin-MTC, dSLIM, dutasteride, edotecarin, eflornithine, exatecan, fenretinide, histamine dihydrochloride, histrelin hydrogel implant, holmium-166 DOTMP, ibandronic acid, interferon gamma, intron-PEG, ixabepilone, keyhole limpet hemocyanin, L-651582, lanreotide, lasofoxifene, libra, lonafarnib, miproxifene, minodronate, MS-209, liposomal MTP-PE, MX-6, nafarelin, nemorubicin, neovastat, nolatrexed, oblimersen, onco-TCS, osidem, paclitaxel polyglutamate, pamidronate disodium, PN-401, QS-21, quazepam, R-1549, raloxifene, ranpirnase, 13-cis-retinoic acid, satraplatin, seocalcitol, T-138067, tarceva, taxoprexin, thalidomide, thymosin alpha 1, tiazofurine, tipifarnib, tirapazamine, TLK-286, toremifene, TransMID-107R, valspodar, vapreotide, vatalanib, verteporfin, vinflunine, Z-100, zoledronic acid or salts thereof.

In an embodiment of the present invention, component C can be one or more of the following: 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766 (RDEA 119), belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, zorubicin. Alternatively, said component C can be one or more further pharmaceutical agents selected from gemcitabine, paclitaxel (when component B is not itself paclitaxel), cisplatin, carboplatin, sodium butyrate, 5-FU, doxirubicin, tamoxifen, etoposide, trastumazab, gefitinib, intron A, rapamycin, 17-MG, U0126, insulin, an insulin derivative, a PPAR ligand, a sulfonylurea drug, an α-glucosidase inhibitor, a biguanide, a PTP-1B inhibitor, a DPP-IV inhibitor, a 11-beta-HSD inhibitor, GLP-1, a GLP-1 derivative, GIP, a GIP derivative, PACAP, a PACAP derivative, secretin or a secretin derivative.

Alternatively, said component C can be one or more pharmaceutical agents selected from: a taxane, such as Docetaxel, Paclitaxel, or Taxol; an epothilone, such as Ixabepilone, Patupilone, or Sagopilone; Mitoxantrone; Predinisolone; Dexamethasone; Estramustin; Vinblastin; Vincristin; Doxorubicin; Adriamycin; Idarubicin; Daunorubicin; Bleomycin; Etoposide; Cyclophosphamide; Ifosfamide; Procarbazine; Melphalan; 5-Fluorouracil; Capecitabine; Fludarabine; Cytarabine; Ara-C; 2-Chloro-2'-deoxyadenosine; Thioguanine; an anti-androgen, such as Flutamide, Cyproterone acetate, or Bicalutamide; Bortezomib; a platinum derivative, such as Cisplatin, or Carboplatin; Chlorambucil; Methotrexate; and Rituximab.

Optional anti-hyper-proliferative agents which can be added as component C to the combination of the salt of the present invention include but are not limited to compounds listed on the cancer chemotherapy drug regimens in the 11th Edition of the Merck Index, (1996), which is hereby incorporated by reference, such as asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other anti-hyper-proliferative agents suitable for use as component C with the combination of the salt of the present invention include but are not limited to those compounds acknowledged to be used in the treatment of neoplastic diseases in *Goodman and Gilman's The Pharmacological Basis of Therapeutics* (Ninth Edition), editor Molinoff et al., publ. by McGraw-Hill, pages 1225-1287, (1996), which is hereby incorporated by reference, such as aminoglutethimide, L-asparaginase, azathioprine, 5-azacytidine cladribine, busulfan, diethylstilbestrol, 2',2'-difluorodeoxycytidine, docetaxel, erythrohydroxynonyl adenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel (when component B is not itself paclitaxel), pentostatin, N-phosphonoacetyl-L-aspartate (PALA), plicamycin, semustine, teniposide, testosterone propionate, thiotepa, trimethylmelamine, uridine, and vinorelbine.

Other anti-hyper-proliferative agents suitable for use as component C with the combination of the salt of the present invention include but are not limited to other anti-cancer agents such as epothilone and its derivatives, irinotecan, raloxifen and topotecan.

Generally, the use of cytotoxic and/or cytostatic agents as component C in combination with the salt of the present invention will serve to:
(1) yield better efficacy in reducing the growth of a tumor or even eliminate the tumor as compared to administration of either agent alone,
(2) provide for the administration of lesser amounts of the administered chemotherapeutic agents,
(3) provide for a chemotherapeutic treatment that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents used alone, compared to known instances where other cancer agent salts produce antagonistic effects.

Biological Section

PI3Kα and PI3Kβ Radioactive Lipid Kinase Assay

The p110α biochemical assay is a radioactive assay measuring the incorporation of $^{33}P$ into the p110α substrate, phosphatidylinsoitol (PI). This assay is a modification of an assay developed at RCK (Fuchikami et al., 2002). A His-tagged N-terminal truncated (ΔN 1-108) p110α and the same truncated p110β (ΔN 1-108) proteins lacking the p85-binding domain was expressed in Sf9 cells and purified to >50% purity. For the generation of $IC_{50}$ curves, the reaction was performed in a 384-well format using MaxiSorp plates under the following conditions. Plates were coated with 2 μg/well of a 1:1 molar ratio of phosphatidylinositol (PI: Avanti #840042C) and phosphatidylserine (PS: Avanti #840032C) diluted in chloroform. The organic solvent was allowed to evaporate by storing plates in the fume hood overnight. Plates were then sealed with mylar plate sealers and stored up to a month at 4° C. until needed. 7.5 ng of truncated purified p110α protein was added to each well, containing 9 μL of reaction buffer (50 mM MOPSO pH7.0, 100 mM NaCl, 4 mM MgCl2, 0.1% (w/v) BSA) except for negative control wells which received reaction buffer only. One microliter of each test compound in DMSO was transferred from stock dilutions to generate an eight-point dose response (0.0, 0.003, 0.01 0.03, 0.1, 0.3, 1.0, 3.0 and 10 μM final BAY compound concentration). Reactions were started by the addition of 5 μL of a 40 μM ATP solution containing 20 μCi/ml [γ-$^{33}$P]-ATP and were allowed to proceed for two hours at room temperature with gentle mixing. Reactions were terminated by the addition of 5 μL of a 25 mM EDTA stock solution. Plates were washed with a 384-well plate washer in buffer without detergent and 25 μL of UltimaGold scintillation cocktail was added to each well. The radioactivity incorporated into the immobilized PI substrate was determined with a BetaPlate Liquid Scintillation Counter. Inhibition was calculated using the following equation:

$$\% \text{ inhibition} = 1 - (T_{cpm} - B_{cpm})/(P_{cpm} - B_{cpm}) \times 100.$$

$T_{cpm}$=$^{33}$P-cpm in presence of test compound
$B_{cpm}$=$^{33}$P-cpm in background control (no enzyme)
$P_{cpm}$=$^{33}$P-cpm in p110 enzyme control (no inhibitor)

The $IC_{50}$ values for the free base and the dihydrochloride salt in the p110α and p110β biochemical assays are summarized in Table A. The two compounds showed similar activities in both PI3Kα and PI3Kβ biochemical assays. Slightly better potency with the dihydrochloride salt form might be due to improved solubility.

TABLE A

Activity of the free base and the dihydrochloride salt in PI3Kα and PI3Kβ assays

| Compound | PI3Kα $IC_{50}$ (M) | PI3Kβ $IC_{50}$ (M) |
|---|---|---|
| Free base | 4.96E−10 | 3.72E−09 |
| Dihydrochloride salt | 1.23E−10 | 1.00E−09 |

Proliferation Assays

Cell proliferation is determined using the Cell Titer-Glo luminescent cell viability kit from Promega (Cat. #G7573) after 72 hours exposure to the drugs. Briefly, cells were plated at 500-1000 cells/well of 384-well plates in 25 μL growth medium. For each cell line assayed, cells were plated into a separate plate for determination of luminescence at the t=0 hours and t=72 hour time points. Following overnight incubation at 37° C., luminescence values for the t=0 samples were determined by adding 25 μL of Cell Titer-Glo solution per well, transferring the plates to an orbital shaker for 10 minutes at room temperature, and then reading the plates on a Wallac Victor2 1420 Multilabel HTS Counter using the luminometry window (maximum light detection is measured at 428 nM). Dose plates for t=72 hour time points were treated with compounds diluted into growth medium in a final volume of 30 μL. Cells were then incubated for 72 hours at 37° C. Luminescence values for the t=72 hour samples were determined by adding 30 μL of Promega CellTiter-Glo solution, placing the cells on a shaker for 10 minutes at room temperature, and then reading the luminescence using a Victor luminometer. For data processing, t=0 values are subtracted from those determined for the t=72 hour time points, for both the treated and untreated samples. Percent differences in luminescence between drug treated and controls are used to determine percent inhibition of growth.

In a panel of 16 tumor cell lines covering 6 cancer indications, both the free base and the dihydrochloride salt showed potent anti-proliferative activities and the difference in the $IC_{50}$ values was less than 3-fold in all the tumor cell lines tested. These data clearly indicated that the dihydrochloride salt retains the antitumor activity of the free base.

TABLE B

Anti-proliferative activity of the free base and the dihydrochloride in tumor cell line proliferation assays

| Cell Line | Tissue | free base IC50 (nM) | dihydrochloride salt $IC_{50}$ (nM) | $IC_{50}$ Ratio |
|---|---|---|---|---|
| KPL4 | Breast | 3 | 3 | 1.0 |
| BT474 | | 5 | 10 | 0.5 |
| T47D | | 6 | 2 | 2.8 |
| BT20 | | 6 | 2 | 3.1 |
| MCF7 | | 27 | 9 | 3.0 |
| MDA-MB-468 | | 760 | 256 | 3.0 |
| SK-Br-3 | | 2 | 1 | 1.5 |
| LNCaP | Prostate | 69 | 67 | 1.0 |
| PC3 | | 100 | 90 | 1.1 |
| Colo205 | Colon | 48 | 110 | 0.4 |
| HT29 | | 27 | 10 | 2.7 |
| HCT116 | | 56 | 72 | 0.8 |
| A549 | Lung | 37 | 44 | 0.8 |
| H460 | | 46 | 67 | 0.7 |
| U87MG | Brain | 85 | 85 | 1.0 |
| 786O | Kidney | 116 | 247 | 0.5 |

REFERENCE

Fuchikami K, Togame H, Sagara A, Satoh T, Gantner F, Bacon K B, Reinemer P. J Biomol Screen. 7(5):441-50 (2002). A versatile high-throughput screen for inhibitors of lipid kinase activity: development of an immobilized phospholipid plate assay for phosphoinositide 3-kinase gamma.

The invention claimed is:

1. A method for the treatment of non-Hodgkin's lymphoma comprising administering to a patient in need thereof a therapeutically effective amount of a 2-amino-N-[7-methoxy-8-(3-morpholin-4-ylpropoxy)-2,3-dihydroimidazo[1,2-c]quinazolin-5-yl]pyrimidine-5-carboxamide dihydrochloride salt or a solvate, hydrate or tautomer thereof.

2. The method according to claim 1, wherein the dihydrochloride salt, or solvate, hydrate or tautomer thereof, is in crystalline form.

3. The method according to claim 1, further comprising administering an additional pharmaceutical agent.

4. The method according to claim 3, wherein the additional pharmaceutical agent is selected from: 131I-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, BAY 86-9766, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta, pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, raloxifene, raltitrexed, ranimustine, razoxane, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, and zorubicin.

* * * * *